United States Patent
Krivoruchko

(10) Patent No.: US 7,297,134 B2
(45) Date of Patent: Nov. 20, 2007

(54) DUAL USE CATHETER

(75) Inventor: Mike Krivoruchko, Forestville, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 930 days.

(21) Appl. No.: 10/132,932

(22) Filed: Apr. 26, 2002

(65) Prior Publication Data

US 2003/0204201 A1 Oct. 30, 2003

(51) Int. Cl.
*A61M 29/00* (2006.01)

(52) U.S. Cl. .................. 604/103.04; 606/192

(58) Field of Classification Search ........... 604/103.04, 604/102.01, 102.02, 101.03, 102.03, 910, 604/912, 921; 606/191, 192, 194
See application file for complete search history.

(56) References Cited

U.S. PATENT DOCUMENTS

| | | | |
|---|---|---|---|
| 4,610,660 A * | 9/1986 | Rosenberg | ............... 604/544 |
| 5,047,045 A | 9/1991 | Arney et al. | |
| 5,409,459 A * | 4/1995 | Gambale | ............... 604/102.02 |
| 5,451,233 A | 9/1995 | Yock | |
| 5,534,007 A * | 7/1996 | St. Germain et al. | ...... 623/1.11 |
| 5,807,355 A * | 9/1998 | Ramzipoor et al. | ......... 604/526 |
| 5,891,110 A | 4/1999 | Larson et al. | |
| 6,050,972 A * | 4/2000 | Zadno-Azizi et al. | .... 604/97.01 |
| 6,540,719 B2 * | 4/2003 | Bigus et al. | ............. 604/96.01 |

* cited by examiner

*Primary Examiner*—Anhtuan T. Nguyen
*Assistant Examiner*—Tuan Van Nguyen
(74) *Attorney, Agent, or Firm*—Serge Hodgson

(57) ABSTRACT

A catheter assembly and method includes a multi-lumen portion having a guide wire lumen and an inflation/deployment lumen. The guide wire lumen includes a distal guide wire lumen portion having a rapid exchange guide wire port, and a proximal guide wire lumen portion rotatable to selectively expose the rapid exchange guide wire port. The inflation/deployment lumen includes a rotatable seal which facilitates rotation of the proximal guide wire lumen portion.

19 Claims, 3 Drawing Sheets

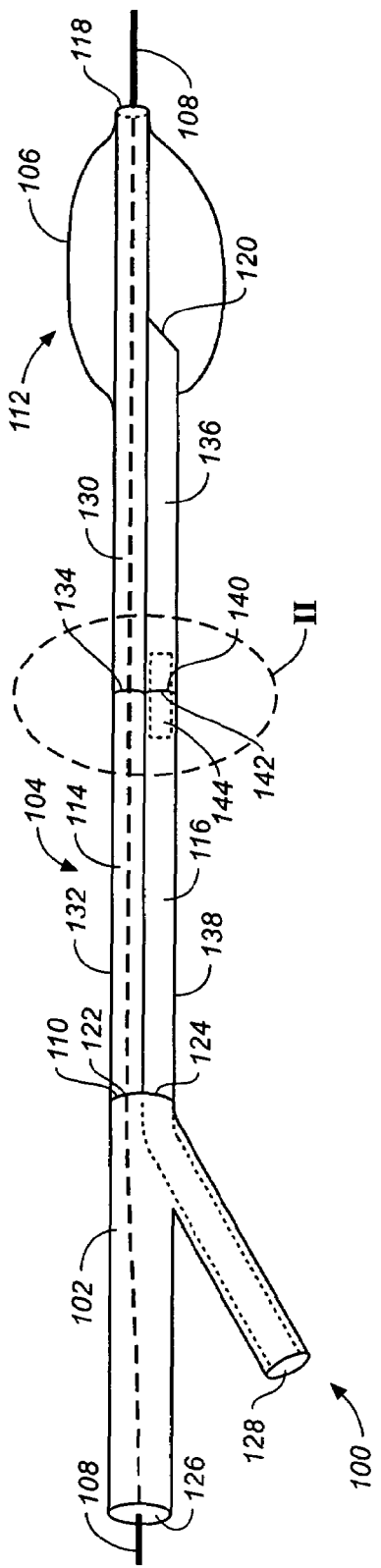
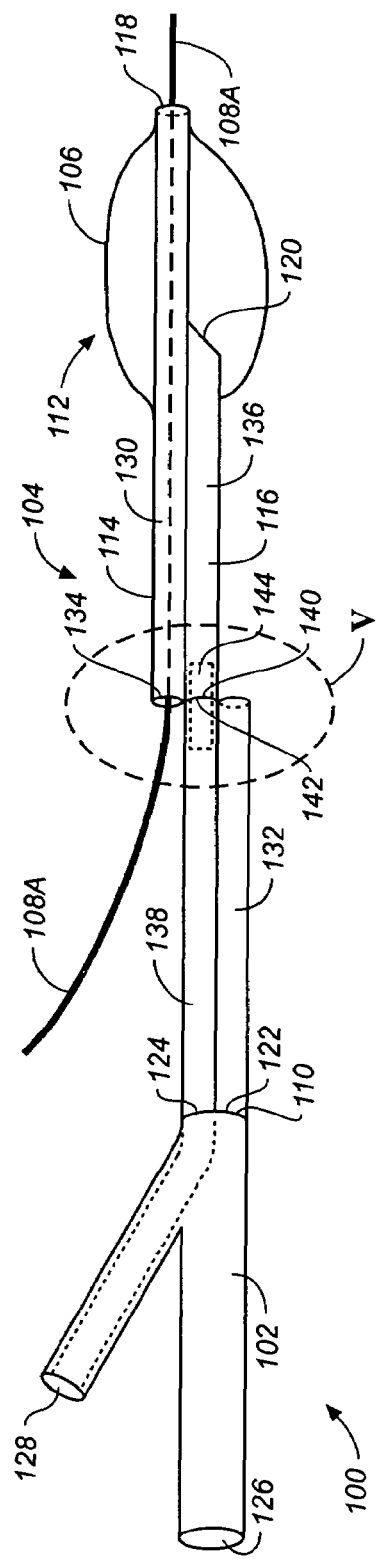
FIG._1
FIG._4

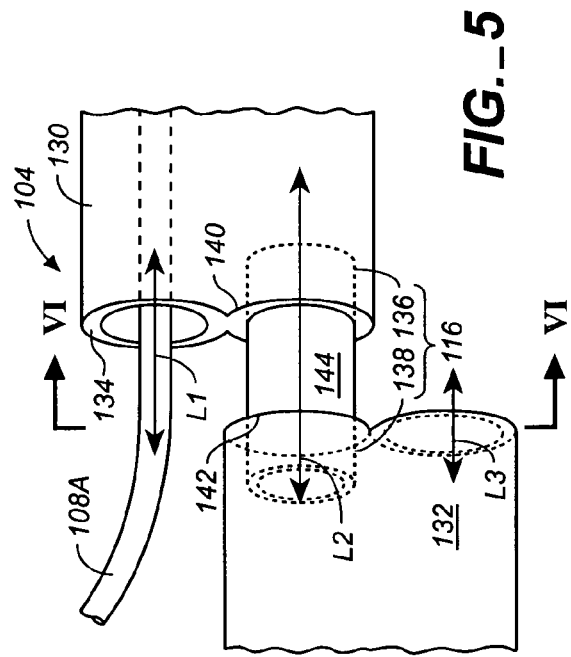
FIG._5
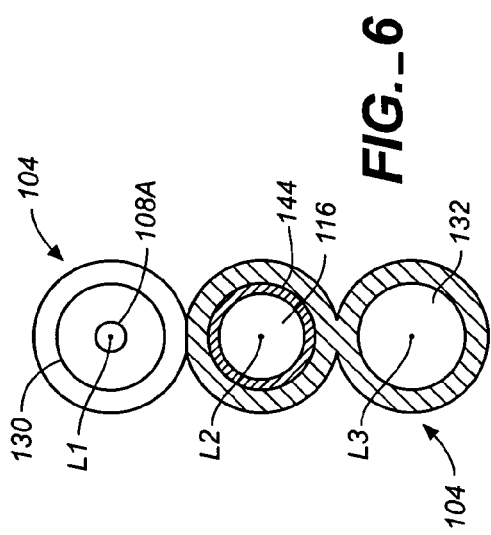
FIG._6
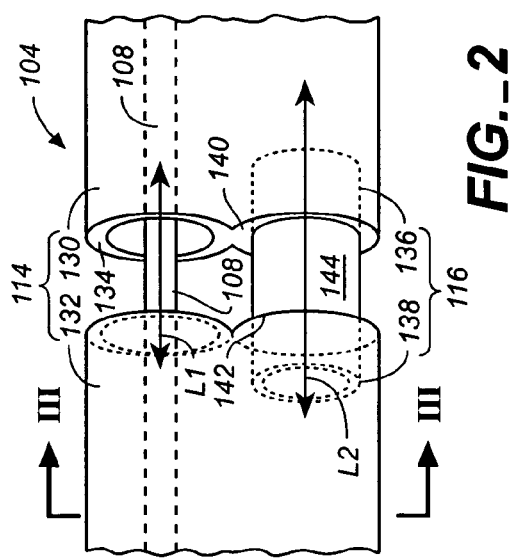
FIG._2
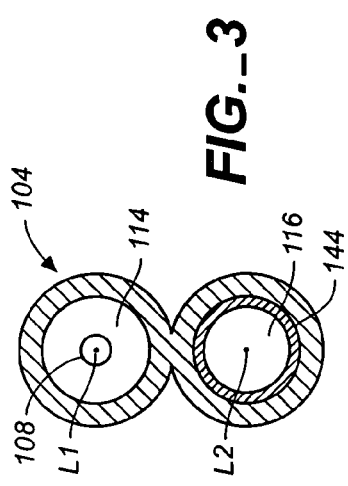
FIG._3

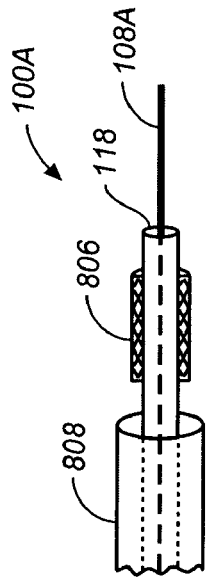
FIG._9
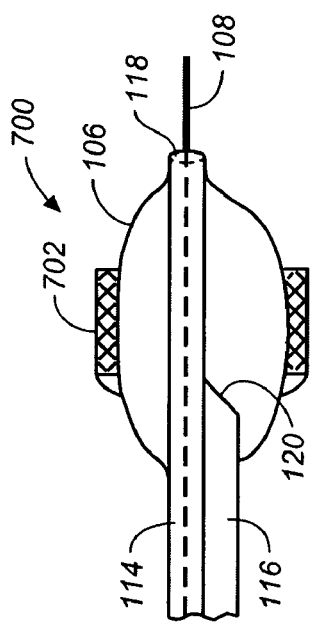
FIG._7
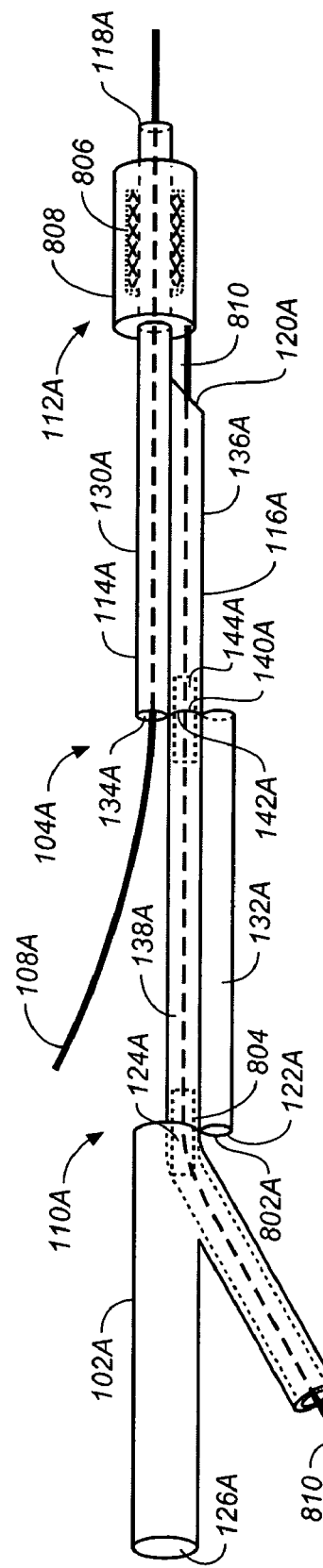
FIG._8

DUAL USE CATHETER

BACKGROUND OF THE INVENTION

1. Field of the Invention

The present invention relates to an intra-vascular device and method. More particularly, the present invention relates to an intra-vascular catheter which can be utilized in a rapid exchange or over-the-wire (OTW) operating mode.

2. Description of the Related Art

Human blood vessels often become occluded or completely blocked by plaque, thrombi, other deposits, embolic or other substances, which reduce the blood carrying capacity of the vessel. Should the blockage occur at a critical place in the circulatory system, serious and permanent injury, or even death, can occur. To prevent this, some form of medical intervention is usually performed when significant occlusion is detected.

Various types of intervention techniques have been developed which facilitate the reduction or removal of the blockage in the blood vessel, allowing increased blood flow through the vessel. One technique for treating occlusion of a blood vessel is the use a dilation catheter having a dilation balloon. However, in practice, is often necessary to exchange one dilation catheter for another.

In doing so, it is often necessary to utilize an over-the-wire (OTW) dilation catheter which uses long exchange wires, e.g., 300 cm exchange wires. However, use of long exchange wires often requires two operators to perform the procedure. During this procedure, it is necessary that the operators communicate with each other which makes the procedure time-consuming. In addition, since the exchange wire is so long, it often is awkward to handle and for that reason may come into contact with the floor or become contaminated which necessitates removing the entire apparatus being utilized for the procedure.

To avoid these difficulties with OTW dilation catheters, rapid exchange dilation catheters have been developed which utilized a relatively short guide wire. The rapid exchange dilation catheter has been widely praised by the medical profession and has met with much commercial success in the marketplace.

However, the OTW dilation catheter is still desirable for use in certain circumstances, for example, when the additional length of the guide wire facilitate positioning or is otherwise desirable. Thus, a dilation catheter that can operate in an over-the-wire mode or a rapid exchange mode would provide needed flexibility for the medical profession.

SUMMARY OF THE INVENTION

In accordance with an embodiment of the present invention, a catheter assembly includes a multi-lumen portion having a guide wire lumen and an inflation/deployment lumen. The guide wire lumen includes a distal guide wire lumen portion having a rapid exchange guide wire port, and a proximal guide wire lumen portion rotatable to selectively expose the rapid exchange guide wire port.

In accordance with one embodiment, the inflation/deployment lumen has a distal inflation/deployment lumen portion; a proximal inflation/deployment lumen portion; and a rotatable seal forming a fluid tight seal between the distal inflation/deployment lumen portion and the proximal inflation/deployment lumen portion.

To configure the catheter assembly for use in an over-the-wire mode, the distal guide wire lumen portion and the proximal guide wire lumen portion are aligned. A guide wire is then passed through the entire length of the guide wire lumen and out through a guide wire lumen port of a handle coupled to the guide wire lumen.

To configure the catheter assembly for use in a rapid exchange mode, the proximal guide wire lumen portion is rotated around the inflation/deployment lumen to expose the rapid exchange guide wire port of the distal guide wire lumen portion. The rotatable seal of the inflation/deployment lumen facilitate this rotation. A guide wire is then passed through just the length of the distal guide wire lumen portion and out through the rapid exchange guide wire port of the distal guide wire lumen portion.

The present invention is best understood by reference to the following detailed description when read in conjunction with the accompanying drawings.

BRIEF DESCRIPTION OF THE DRAWINGS

FIG. 1 is a side plan view, in partial cross-section, of a dual use catheter in accordance with one embodiment of the present invention;

FIG. 2 is an enlarged view of the region II of the catheter of FIG. 1;

FIG. 3 is a cross-sectional view of the catheter taken at III-III of FIG. 2;

FIG. 4 is a side plan view, in partial cross-section, of a dual use catheter in accordance with another embodiment of the present invention;

FIG. 5 is an enlarged view of the region V of the catheter of FIG. 4;

FIG. 6 is a cross-sectional view of the catheter taken at VI-VI of FIG. 5;

FIG. 7 is a perspective view, in partial cross-section, of a dilation balloon assembly in accordance with one embodiment of the present invention;

FIG. 8 is a side plan view, in partial cross-section, of a dual use catheter in accordance with another embodiment of the present invention; and FIG. 9 is a perspective view, partially in cross-section, of the deployment of a stent of FIG. 8 in accordance with one embodiment of the present invention.

Common reference numerals are used throughout the drawings and detailed description to indicate like elements.

DETAILED DESCRIPTION

FIG. 1 is a side plan view, in partial cross-section, of a dual use catheter 100 in accordance with one embodiment of the present invention. Referring now to FIG. 1, catheter 100, sometimes called a catheter assembly, includes a handle 102, a multi-lumen portion 104, a dilation balloon 106 and a guide wire 108. More particularly, handle 102 is mounted to a proximal end 110 of multi-lumen portion 104 and dilation balloon 106 is mounted at a distal end 112 of multi-lumen portion 104.

Multi-lumen portion 104 includes a guide wire lumen 114 and a deployment/inflation lumen 116 in a side-by-side arrangement. Dilation balloon 106 is mounted around guide wire lumen 114 adjacent a distal end 118 of guide wire lumen 114.

Deployment/inflation lumen 116, sometimes called an inflation lumen 116, terminates inside of dilation balloon 106 at a distal end 120 of inflation lumen 116. Accordingly, inflation lumen 116 is in fluid communication with dilation balloon 106.

Proximal ends 122, 124 of guide wire lumen 114 and inflation lumen 116, respectively, are mounted to handle 102 using any one of a number of techniques well known to those of skill in the art.

Handle 102 includes an over-the-wire (OTW) guide wire lumen port 126 and an inflation/deployment lumen port 128, sometimes called an inflation lumen port 128. Guide wire lumen port 126 is in communication with guide wire lumen 114. Inflation lumen port 128 is in fluid communication with inflation lumen 116 and thus with dilation balloon 106.

In accordance with this embodiment, catheter 100 is configured for use in an over-the-wire mode. Accordingly, guide wire 108 enters guide wire lumen 114 at distal end 118, extends through guide wire lumen 114 to handle 102, extends through handle 102, and exits at guide wire lumen port 126.

FIG. 2 is an enlarged view of the region II of catheter 100 of FIG. 1 in accordance with one embodiment of the present invention. FIG. 3 is a cross-sectional view of catheter 100 taken at III-III of FIG. 2.

Referring now to FIGS. 1, 2 and 3 together, guide wire lumen 114 includes a distal guide wire lumen portion 130 and a proximal guide wire lumen portion 132. Distal guide wire lumen portion 130 extends between distal end 118 of guide wire lumen 114 and a rapid exchange guide wire port 134 of distal guide wire lumen portion 130.

When catheter 100 is used in the over-the-wire mode, distal guide wire lumen portion 130 and proximal guide wire lumen portion 132 are aligned. More particularly, distal guide wire lumen portion 130 and proximal guide wire lumen portion 132 share a common longitudinal axis L1 such that distal guide wire lumen portion 130 and proximal guide wire lumen portion 132 operate as if guide wire lumen 114 is a single unitary lumen.

Inflation lumen 116 includes a distal inflation/deployment lumen portion 136, sometimes called a distal inflation lumen portion 136, and a proximal inflation/deployment lumen portion 138, sometimes called a proximal inflation lumen portion 138. Distal inflation lumen portion 136 extends proximally from distal end 120 of inflation lumen 116 to a proximal end 140 of distal inflation lumen portion 136. Proximal inflation lumen portion 138 extends distally from handle 102 to a distal end 142 of proximal inflation lumen portion 138.

Distal inflation lumen portion 136 and proximal inflation lumen portion 138 are mounted together by a rotatable seal 144 of inflation lumen 116. More particularly, distal end 142 of proximal inflation lumen portion 138 is mounted to proximal end 140 of distal inflation lumen portion 136 by rotatable seal 144.

Proximal inflation lumen portion 138 and distal inflation lumen portion 136 are aligned. More particularly, proximal inflation lumen portion 138 and distal inflation lumen portion 136 share a common longitudinal axis L2.

Rotatable seal 144 forms a fluid tight seal between proximal inflation lumen portion 138 and distal inflation lumen portion 136. Rotatable seal 144 allows proximal inflation lumen portion 138 to be rotated around longitudinal axis L2 relative to distal inflation lumen portion 136 without compromising the fluid tight seal. Accordingly, proximal inflation lumen portion 138 can be rotated relative to distal inflation lumen portion 136 without leakage of fluid between proximal inflation lumen portion 138 and distal inflation lumen portion 136.

Referring again to FIG. 1, during use, guide wire 108 is introduced intra-vascularly and guided to the treatment side of a patient, e.g., a restriction such as an occlusion of a vessel. Guide wire 108 is then fed, sometimes called passed, through distal end 118 of guide wire lumen 114, through distal guide wire lumen portion 130, through proximal guide wire lumen portion 132, through handle 102 and out through guide wire lumen port 126 of handle 102 as illustrated in FIG. 1.

Dilation balloon 106 is advanced over guide wire 108 and thus guided to the treatment site. Dilation balloon 106 can include radiopaque markers to facilitate observation and positioning of dilation balloon 106.

Once located at the treatment site, dilation balloon 106 is inflated through inflation lumen port 128 of handle 102 to open the restriction in the vessel. Illustratively, a pressurized fluid is introducing through inflation lumen port 128 of handle 102 to inflate dilation balloon 106. Dilation balloon 106 is then deflated and withdrawn from the patient.

FIG. 4 is a side plan view, in partial cross-section, of dual use catheter 100 in accordance with another embodiment of the present invention. Referring now to FIG. 4, in accordance with this embodiment, catheter 100 is configured for use in a rapid exchange mode. Accordingly, a guide wire 108A enters guide wire lumen 114 at distal end 118, extends through distal guide wire lumen portion 130 and exits at rapid exchange guide wire port 134. This allows guide wire 108A to be relatively short, e.g., 180 cm, and more particularly, to be shorter than guide wire 108 of FIG. 1, e.g., 300 cm.

FIG. 5 is an enlarged view of the region V of catheter 100 of FIG. 4 in accordance with one embodiment of the present invention. FIG. 6 is a cross-sectional view of catheter 100 taken at VI-VI of FIG. 5.

Referring now to FIGS. 4, 5, and 6 together, when catheter 100 is used in the rapid exchange mode, distal guide wire lumen portion 130 and proximal guide wire lumen portion 132 are offset, sometimes called un-aligned. More particular, distal guide wire lumen portion 130 has a longitudinal axis Li which is parallel to and offset from a longitudinal axis L3 of proximal guide wire lumen portion 132.

To use catheter 100 in the rapid exchange mode, proximal guide wire lumen portion 132 is rotated around inflation lumen 116 with respect to distal guide wire lumen portion 130 and moved out of the way. Thus, proximal guide wire lumen portion 132 is rotated to selectively expose rapid exchange guide wire port 134. For example, handle 102 is rotated to rotate proximal guide wire lumen portion 132. This exposes rapid exchange guide wire port 134 of distal guide wire lumen portion 130.

Rotation of proximal guide wire lumen portion 132 also rotates proximal inflation lumen portion 138 relative to distal inflation lumen portion 136. However, rotatable seal 144 facilitate this rotation without compromising the seal and the axial connection between proximal inflation lumen portion 138 and distal inflation lumen portion 136 as discussed above.

Referring again to FIG. 4, during use, guide wire 108A is introduced intra-vascularly and guided to the treatment side of a patient, e.g., a restriction such as an occlusion of a vessel. Guide wire 108A is then fed through distal end 118 of distal guide wire lumen portion 130, though distal guide wire portion 130, and out through rapid exchange guide wire port 134 as illustrated in FIG. 4.

Dilation balloon 106 is advanced over guide wire 108A and thus guided to the treatment site. Dilation balloon 106 can include radiopaque markers to facilitate observation and positioning a dilation balloon 106.

Once located at the treatment site, dilation balloon 106 is inflated through inflation lumen port 128 of handle 102 to open the restriction in the vessel. Illustratively, a pressurized fluid is introducing through inflation lumen port 128 of handle 102 to inflate dilation balloon 106. Dilation balloon 106 is then deflated and withdrawn from the patient.

As discussed above, inflation of dilation balloon 106 opens the restriction in the vessel. However, in certain applications such as when it is desirable to prevent subsequent collapse of the vessel, a stent is employed with dilation balloon 106 as discussed in greater detail below with reference to FIG. 7.

FIG. 7 is a perspective view, in partial cross-section, of a dilation balloon assembly 700 in accordance with one embodiment of the present invention. Dilation balloon assembly 700 includes dilation balloon 106 and a stent 702.

Stent 702 is located on and around dilation balloon 106. Inflation of dilation balloon 106 as discussed above likewise expands stent 702 and anchors stent 702 within the vessel at the treatment site. Dilation balloon 106 is then deflated and withdrawn from the patient. However, stent 702 remains at the treatment side and prevents or minimizes subsequent collapse or obstruction of the vessel.

FIG. 8 is a side plan view, in partial cross-section, of a dual use catheter 100A in accordance with another embodiment of the present invention. Catheter 100A of FIG. 8 is similar to catheter 100 of FIG. 4 and only the significant differences are discussed below.

Referring now to FIG. 8, in accordance with this embodiment, catheter 100A is used in a rapid exchange mode. Accordingly, guide wire 108A enters distal guide wire lumen portion 130A at distal end 118A, extends through distal guide wire lumen portion 130A and exits at rapid exchange guide wire port 134A.

However, in accordance with this embodiment, a proximal guide wire lumen portion 132A of guide wire lumen 114 is rotated to expose rapid exchange guide wire port 134A of distal guide wire lumen portion 130A without rotation of handle 102A.

In accordance with this embodiment, proximal guide wire lumen portion 132A includes a proximal end 802A, which is detached from handle 102A. This allows proximal guide wire lumen portion 132A to be rotated around inflation/deployment lumen 116 without rotation of handle 102A.

Rotation of proximal guide wire lumen portion 132A also rotates proximal inflation lumen portion 138A relative to distal inflation lumen portion 136A and also relative to handle 102A. However, rotatable seal 144A, sometimes called a first rotatable seal, facilitate this rotation relative to distal inflation lumen portion 136A without compromising the seal between proximal inflation lumen portion 138A and distal inflation lumen portion 136A similar to that discussed above. Other numbered items pictured having an "A" suffix are similar in structure to similarly numbered items discussed above without the "A" suffix.

To facilitate rotation of proximal inflation lumen portion 138A relative to handle 102A, a rotatable seal 804, sometimes called a second rotatable seal, forms a fluid tight seal (although where no fluid tightness is required to facilitate balloon pressurization, a rotatable axially secure mechanical connection is also to be considered synonymous with a fluid tight seal) between proximal inflation lumen portion 138A and handle 102A. Rotatable seal 804 allows proximal inflation lumen portion 138A to be rotated around its longitudinal axis relative to handle 102A without compromising the fluid tight seal and/or the mechanical connection there between. Accordingly, proximal inflation lumen portion 138A can be rotated relative to handle 102A without leakage of fluid between proximal inflation lumen portion 138A and handle 102A.

Also in accordance with this embodiment, catheter 100A employs a self-expanding stent 806. More particularly, distal guide wire lumen portion 130A performs as a pushrod. Stent 806A is placed around distal guide wire lumen portion 130A adjacent distal end 118A.

A sheath 808 radially compresses and restrains from extending stent 806. Sheath 808 is connected to a sheath retraction wire 810.

Sheath retraction wire 810 enters distal end 120A of lumen 116A, passes through lumen 116A, through handle 102A, and exits through inflation lumen port 128A of handle 102A.

FIG. 9 is a perspective view, partially in cross-section, of the deployment of stent 806 of FIG. 8 in accordance with one embodiment of the present invention. Referring now to FIGS. 8 and 9 together, sheath retraction wire 810 is retracted (pulled) out of inflation lumen port 128 to retract sheath 808 and to deploy stent 806 as shown in FIG. 9.

Upon deployment, stent 806 self-expands and anchors within the vessel at the treatment site. Catheter 100A is then withdrawn from the patient. However, stent 806 remains at the treatment side and prevents or minimizes subsequent collapse or obstruction of the vessel.

An embodiment according to the invention includes a method of configuring a catheter assembly for use in an over-the-wire mode including the steps of aligning a distal guide wire lumen portion of a guide wire lumen with a proximal guide wire lumen portion of the guide wire lumen and passing a guide wire through a distal end of the guide wire lumen, through the distal guide wire lumen portion and through the proximal guide wire lumen portion. Where the step of passing a guide wire through a distal end of the guide wire lumen includes passing the guide wire through a handle and out through a guide wire lumen port of the handle. A method of configuring a catheter assembly for use in a rapid exchange mode includes rotating a proximal guide wire lumen portion around an inflation/deployment lumen to expose a rapid exchange guide wire port of a distal guide wire lumen portion of a guide wire lumen and passing a guide wire through a distal end of the distal guide wire lumen portion, through the distal guide wire lumen portion and out through the rapid exchange guide wire port, where the inflation/deployment lumen includes a distal inflation/deployment lumen portion, a proximal inflation/deployment lumen portion, and a rotatable seal forming a fluid tight seal between the distal inflation/deployment lumen portion and the proximal inflation/deployment lumen portion. The step of rotating includes rotating the proximal inflation/deployment lumen portion relative to the distal inflation/deployment lumen portion relative to a longitudinal axis of the catheter.

This disclosure provides exemplary embodiments of the present invention. The scope of the present invention is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A catheter assembly comprising:
   a multi-lumen portion comprising a guide wire lumen and an inflation/deployment lumen,
   wherein said guide wire lumen comprises:

a distal guide wire lumen portion comprising a rapid exchange guide wire port; and a proximal guide wire lumen portion rotatable around said inflation/deployment lumen to offset said proximal guide wire lumen portion from said distal guide wire lumen portion to selectively expose said rapid exchange guide wire port; and wherein said inflation/deployment lumen comprises:

a distal inflation/deployment lumen portion;

a proximal inflation/deployment lumen portion; and a rotatable seal rotatably mounting said distal inflation/deployment lumen portion to said proximal inflation/deployment lumen portion; and wherein a longitudinal axis of said distal guide wire lumen portion is parallel to and offset from a longitudinal axis of said proximal guide wire lumen portion when said proximal guide wire lumen portion is offset from said distal guide wire lumen portion.

2. The catheter assembly of claim 1 further comprising a dilation balloon mounted around said guide wire lumen adjacent a distal end of said guide wire lumen.

3. The catheter assembly of claim 2 wherein said inflation/deployment lumen is in fluid communication with said dilation balloon.

4. The catheter assembly of claim 2 wherein said inflation/deployment lumen comprises a distal end inside of said dilation balloon.

5. That catheter assembly of claim 2 further comprising a stent located on and around said dilation balloon.

6. The catheter assembly of claim 1 further comprising a handle comprising:

an over-the-wire guide wire lumen port in communication with said guide wire lumen; and an inflation/deployment lumen port in fluid communication with said inflation/deployment lumen.

7. The catheter assembly of claim 6 further comprising a guide wire entering said guide wire lumen at a distal end of said guide wire lumen, extending through said guide wire lumen to said handle, extending through said handle and exiting at said over-the-wire guide wire lumen port.

8. The catheter assembly of claim 7 wherein said catheter assembly is configured in an over-the-wire mode.

9. The catheter assembly of claim 7 wherein said distal guide wire lumen portion and said proximal guide wire lumen portion are aligned.

10. The catheter assembly of claim 1 further comprising a guide wire entering said distal guide wire lumen portion at a distal end of said guide wire lumen, extending through distal guide wire lumen portion and exiting at said rapid exchange guide wire lumen port.

11. The catheter assembly of claim 10 wherein said catheter assembly is configured in a rapid exchange mode.

12. The catheter assembly of claim 1 wherein said distal guide wire lumen portion and said proximal guide wire lumen portion are offset, said catheter assembly further comprising:

a guide wire entering said distal guide wire lumen portion at a distal end of said guide wire lumen, extending through said distal guide wire lumen portion and exiting at said rapid exchange guide wire lumen port.

13. The catheter assembly of claim 1 farther comprising:

a stent around said distal guide wire lumen portion adjacent a distal end of said guide wire lumen;

a sheath radially compressing and restraining said stent; and a sheath retraction wire connected to said sheath.

14. The catheter assembly of claim 13 wherein said sheath retraction wire extends through said inflation/deployment lumen.

15. The catheter assembly of claim 1 further comprising a dilation balloon in fluid communication with said inflation/deployment lumen.

16. The catheter assembly of claim 1 further comprising a handle comprising an inflation/deployment lumen port in fluid communication with said inflation/deployment lumen.

17. The catheter assembly of claim 16 further comprising a second rotatable seal forming a fluid tight seal between said proximal inflation/deployment lumen portion and said handle.

18. The catheter assembly of claim 9 wherein said distal guide wire lumen portion and said proximal guide wire lumen portion share a common longitudinal axis.

19. A catheter assembly comprising:

a multi-lumen portion comprising a guide wire lumen and an inflation/deployment lumen, wherein said guide wire lumen comprises:

a distal guide wire lumen portion comprising a rapid exchange guide wire port; and a proximal guide wire lumen portion rotatable to selectively expose said rapid exchange guide wire port; and wherein said inflation/deployment lumen comprises:

a distal inflation/deployment lumen portion;

a proximal inflation/deployment lumen portion; and a rotatable seal forming a fluid tight seal between said distal inflation/deployment lumen portion and said proximal inflation/deployment lumen portion, wherein said proximal guide wire lumen portion is rotated around said proximal inflation/deployment lumen portion to offset said proximal guide wire lumen portion form said distal guide wire lumen portion; and wherein a longitudinal axis of said distal guide wire lumen portion is parallel to and offset from a longitudinal axis of said proximal guide wire lumen portion when said proximal guide wire lumen portion is offset from said distal guide wire lumen portion, and wherein said distal guide wire lumen portion and said proximal guide wire lumen portion share a common longitudinal axis when said proximal guide wire lumen portion is aligned with said distal guide wire lumen portion.

* * * * *

UNITED STATES PATENT AND TRADEMARK OFFICE
CERTIFICATE OF CORRECTION

| | |
|---|---|
| PATENT NO. | : 7,297,134 B2 |
| APPLICATION NO. | : 10/132932 |
| DATED | : November 20, 2007 |
| INVENTOR(S) | : Mike Krivoruchko |

Page 1 of 1

It is certified that error appears in the above-identified patent and that said Letters Patent is hereby corrected as shown below:

Column 8, line 5 claim, "13. The catheter assembly on claim 1 farther comprising:" should be changed to --13. The catheter assembly on claim 1 further comprising--

Signed and Sealed this

Second Day of December, 2008

JON W. DUDAS
*Director of the United States Patent and Trademark Office*